United States Patent [19]

Koerwer

[11] 4,276,080
[45] Jun. 30, 1981

[54] PHENOXY-PHENOXYALKANE CARBOXYLIC ACIDS AND DERIVATIVES AS SUGAR ENHANCERS FOR PLANTS

[75] Inventor: John F. Koerwer, Perkasie, Pa.

[73] Assignee: Union Carbide Corporation, New York, N.Y.

[21] Appl. No.: 133,847

[22] Filed: Mar. 25, 1980

[51] Int. Cl.³ .............................................. A01N 37/38
[52] U.S. Cl. ...................................... 71/108; 71/109; 71/116
[58] Field of Search ........................... 71/108, 109, 116

[56] References Cited

U.S. PATENT DOCUMENTS

| 3,954,442 | 5/1976 | Becker et al. | 71/108 |
| 4,070,177 | 1/1978 | Nishiyama et al. | 71/108 X |

*Primary Examiner*—Catherine L. Mills
*Attorney, Agent, or Firm*—William Raymond Moran

[57] ABSTRACT

A method for increasing the sugar content of plants by applying to such plants an effective amount of a phenoxy-phenoxyalkane carboxylic acid or derivative thereof.

36 Claims, No Drawings

PHENOXY-PHENOXYALKANE CARBOXYLIC ACIDS AND DERIVATIVES AS SUGAR ENHANCERS FOR PLANTS

FIELD OF THE INVENTION

This invention relates to a novel method for increasing the sugar content of plants by applying to such plants an effective amount of a phenoxy-phenoxyalkane carboxylic acid or derivative thereof.

BACKGROUND OF THE INVENTION

Certain phenoxy-phenoxyalkane carboxylic acids and derivatives thereof are disclosed in U.S. Pat. No. 3,954,442 to exhibit an excellent selective herbicidal effect against weed grasses in crop plants but to affect broad-leafed plants to only a small extent. Said patent further discloses that such compounds do not damage crop grasses and can be used to combat weed grasses in such crops as well as in dicotyledonus crop plants.

U.S. Pat. No. 4,070,177, on the other hand, discloses phenoxy-phenoxyalkane carboxylic acids and derivatives thereof having herbicidal action to control the growth of broad-leafed weeds in gramineous crops.

However, neither patent discloses any other biological action of such compounds. In particular neither patent discloses the use of such compounds to increase the sugar content of plants such as sugarcane (*Saccharum officinerum*) or sorghum (*Sorghum vulgare*). Increased sugar content, of course, increases the value of such plants.

SUMMARY OF THE INVENTION

In accordance with the present invention, it has now been discovered that certain phenoxy-phenoxyalkane carboxylic acids and derivatives thereof can be employed to increase the sugar content of plants when applied to such plants from 1 to 7 weeks prior to harvesting in an amount insufficient to exert a herbicidal effect. As a result, an earlier accumulation and significant increase in the sugar content of plants such as sugarcane (*Saccharum officinerum*) and sorghum (*Sorghum vulgare*) can be effected. The resulting plants are of greater value, of course, than the untreated plants.

DETAILED DESCRIPTION OF THE INVENTION

The phenoxy-phenoxyalkane carboxylic acids and derivatives useful as plant sugar enhancers according to the present invention can be represented by the formula

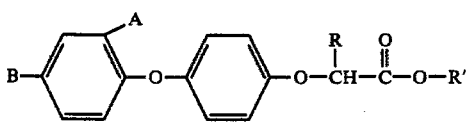

wherein:
A is a hydrogen atom or halogen atom,
B is a hydrogen atom or a halogen atom,
R is a hydrogen atom or a methyl group, and
R' is a hydrogen atom, an alkyl group having from 1 to 4 carbon atoms, or a cation;
provided, however, that either A or B must be a halogen atom.

When R' is an alkyl group in the above formula, it can be either straight or branched chain, e.g., methyl, ethyl, isopropyl, tert.-butyl, and the like, and may be substituted with one or more of a variety of substituents, such as halogen or hydroxyl. When halogen is present, it is preferably chlorine. When R' represents a cation in the formula, it is preferably an ammonium radical, an alkali metal, or an alkaline earth metal, but can be any other agriculturally acceptable cation.

The phenoxy-phenoxyalkane carboxylic acids and phenoxy-phenoxyalkane carboxylic acid derivatives employed in the present invention are known compounds and can be prepared by conventional synthesis methods well known to those skilled in the art. The preparation of such compounds is disclosed, for example, in U.S. Pat. No. 3,954,442 and German Offenlegungsschrift No. 1,668,896, which are hereby incorporated herein by reference.

The compounds employed as plant sugar enhancers in the method of this invention are applied to the plant from 1 to 7 weeks prior to harvesting, preferably from 3 to 5 weeks prior to harvesting. Such compounds should be applied in an amount sufficient to increase the sugar content of the plant, i.e., an effective amount should be employed. As mentioned hereinbefore, however, the amount employed should be insufficient to exert a herbicidal effect on the plant. The proper amount is determined by and dependent upon such factors as the particular compound employed, the method of application, the particular plant species, the state and condition of growth of the plant, and the climatic conditions. Generally, from about ⅛ lb./acre to about 2 lbs./acre, preferably from about ¼ lb./acre to about 1 lb./acre, are employed.

The phenoxy-phenoxyalkane carboxylic acids or derivatives employed in the method of this invention can be applied to mature plants in any suitable form, e.g., as solutions, emulsions, suspensions, dust formulations, and the like. Such compositions generally contain the active compound in an amount of from about 0.06 percent by weight to about 26 percent by weight, preferably from about 0.6 percent by weight to about 1.2 percent by weight. Both liquid compositions and dust formulations may be conveniently applied from either a ground rig or from an aircraft.

The preferred carrier for the active compounds employed in the method of this invention is water. When the active compound is water-soluble, it can be simply dissolved in an amount of water sufficient to give the desired concentration and sprayed on the plants. If desired, a suitable wetting agent may be added to the solution to improve wetting of the foliage and to increase the penetration of the solution into the tissue of the plant. Preferred wetting agents include anionic or nonionic surfactants such as sodium alkysulfates, sodium alkylbenzenesulfonates, sodium ligninsulfonates, polyoxyethylene lauryl ethers, polyoxyethylene alkylaryl ethers, polyoxyethylene fatty acid esters, and polyoxyethylene sorbitan fatty acid esters. Such wetting agents generally do not exceed 1 percent by volume of the final spray solution, and preferably comprise about 0.1 percent to about 0.5 percent of the final spray volume.

Those active compounds which are not sufficiently water-soluble for conventional formulation into aqueous solutions can be prepared as liquid emulsions by dissolving the compounds in a small amount of an agriculturally acceptable solvent and then adding an emulsifier and water. Suitable solvents include n-hexane, toluene, xylene, naphtha, isophorone, dimethylformamide, and the like. Hydrocarbon oils, including paraffin oils, aromatic oils and asphaltic oils, can also be employed, although highly-aromatic oils are preferred, particularly highly-aromatic petroleum-base oils. Suitable emulsifiers include sodium ligninsulfonate, sodium 2,2'-dinaphthylmethane-6,6'-disulfonate, sodium dibutylsulfonate, and sodium oleylmethyllaurate.

Alternatively, these compounds may be formulated into wettable powders which can be dispersed in water by compounding them with conventional excipients such as fillers, wetting agents, dispersing agents, and the like. The wetting agents and emulsifiers mentioned above can be employed in this application. Suitable fillers include vermiculite, attaclay, talc, diatomaceous earth, pyrophillite, kaolin, bentonite and the like.

If desired, the active compounds employed in the method of this invention can be compounded with finely-divided, solid excipients, such as those named above, and applied to the plants as a dust formulation.

If desired, two or more active compounds can be employed in the method of the present invention. Should an admixture be employed, there is no prescribed ratio in which each particular compound must be present. The concentration of the admixture need only be within the concentration range of active material prescribed herein, and the rate of application of the admixture should be within the effective range prescribed herein.

The following examples are set forth for purposes of illustration so that those skilled in the art may better understand the invention. It should be understood, however, that they are exemplary only, and should not be construed as limiting this invention in any manner.

EXAMPLE 1

Methyl 2-[4-(2,4-dichlorophenoxy)phenoxy]propionate was applied to high sucrose sorghum (variety-Ramada) at the eight (8) leaf stage of growth at the rate of 8 ounces acid equivalent of compound per acre. Application was made by spraying 10 ml. of an aqueous emulsion of such compound upon 5 stalks of sorghum (a rate of 100 gallons per acre). The emulsion was prepared by dissolving this compound and a surfactant in a solvent and diluting the solution with water to a final volume of 10 ml.

The sorghum was harvested 12 days after such treatment. The sap of each stalk was then analyzed for brix by means of a refractometer and for reducing sugars using Benedict's copper reduction reaction. Sucrose content was then calculated from the difference between these values. The plants had an average sugar content of 7.0 percent compared to 5.3 percent for like untreated sorghum.

What is claimed is:

1. A method for increasing the sugar content of plants which comprises applying to such plants from 1 to 7 weeks prior to harvesting an effective amount of a compound of the formula

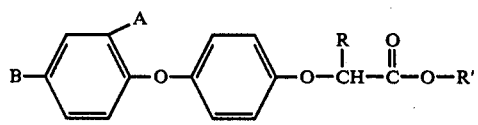

wherein:
A is a hydrogen atom or a halogen atom,
B is a hydrogen atom or a halogen atom,
R is a hydrogen atom or a methyl group, and
R' is a hydrogen atom, an alkyl group having from 1 to 4 carbon atoms, or a cation;
provided, however, that either A or B must be a halogen atom.

2. A method as in claim 1 wherein application is made at a rate of from ⅛ lb./acre to 2 lbs./acre.

3. A method as in claim 1 wherein application is made at a rate of from ¼ lb./acre to 1 lb./acre.

4. A method as in claim 1 wherein the compound is methyl 2-[4-(2,4-dichlorophenoxy)phenoxy]propionate.

5. A method as in claim 4 wherein application is made at a rate of from ⅛ lb./acre to 2 lbs./acre.

6. A method as in claim 4 wherein application is made at a rate of from ¼ lb./acre to 1 lb./acre.

7. A method as in claim 1 wherein the plants are sugarcane plants.

8. A method as in claim 7 wherein application is made at a rate of from ⅛ lb./acre to 2 lbs./acre.

9. A method as in claim 7 wherein application is made at a rate of from ¼ lb./acre to 1 lb./acre.

10. A method as in claim 7 wherein the compound is methyl 2-[4-(2,4-dichlorophenoxy)phenoxy]propionate.

11. A method as in claim 10 wherein application is made at a rate of from ⅛ lb./acre to 2 lbs./acre.

12. A method as in claim 10 wherein application is made at a rate of from ¼ lb./acre to 1 lb./acre.

13. A method as in claim 1 wherein the plants are sorghum plants.

14. A method as in claim 13 wherein application is made at a rate of from ⅛ lb./acre to 2 lbs./acre.

15. A method as in claim 13 wherein application is made at a rate of from ¼ lb./acre to 1 lb./acre.

16. A method as in claim 13 wherein the compound is methyl 2-[4-(2,4-dichlorophenoxy)phenoxy]propionate.

17. A method as in claim 16 wherein application is made at a rate of from ⅛ lb./acre to 2 lbs./acre.

18. A method as in claim 16 wherein application is made at a rate of from ¼ lb./acre to 1 lb./acre.

19. A method as in claim 1 wherein application is made from 3 to 5 weeks prior to harvesting.

20. A method as in claim 19 wherein application is made at a rate of from ⅛ lb./acre to 2 lbs./acre.

21. A method as in claim 19 wherein application is made at a rate of from ¼ lb./acre to 1 lb./acre.

22. A method as in claim 19 wherein the compound is methyl 2-[4-(2,4-dichlorophenoxy)phenoxy]propionate.

23. A method as in claim 22 wherein application is made at a rate of from ⅛ lb./acre to 2 lbs./acre.

24. A method as in claim 22 wherein application is made at a rate of from ¼ lb./acre to 1 lb./acre.

25. A method as in claim 19 wherein the plants are sugarcane plants.

26. A method as in claim 25 wherein application is made at a rate of from ⅛ lb./acre to 2 lbs./acre.

27. A method as in claim 25 wherein application is made at a rate of from ¼ lb./acre to 1 lb./acre.

28. A method as in claim 25 wherein the compound is methyl 2-[4-(2,4-dichlorophenoxy)phenoxy]propionate.

29. A method as in claim 28 wherein application is made at a rate of from ⅛ lb./acre to 2 lbs./acre.

30. A method as in claim 28 wherein application is made at a rate of from ¼ lb./acre to 1 lb./acre.

31. A method as in claim 19 wherein the plants are sorghum plants.

32. A method as in claim 31 wherein application is made at a rate of from ⅛ lb./acre to 2 lbs./acre.

33. A method as in claim 31 wherein application is made at a rate of from ¼ lb./acre to 1 lb./acre.

34. A method as in claim 31 wherein the compound is methyl 2-[4-(2,4-dichlorophenoxy)phenoxy]propionate.

35. A method as in claim 34 wherein application is made at a rate of from ⅛ lb./acre to 2 lbs./acre.

36. A method as in claim 34 wherein application is made at a rate of from ¼ lb./acre to 1 lb./acre.

* * * * *